United States Patent [19]

Chang et al.

[11] 4,052,479
[45] * Oct. 4, 1977

[54] CONVERSION OF METHANOL TO OLEFINIC COMPONENTS

[75] Inventors: Clarence D. Chang, Princeton; William H. Lang, Pennington, both of N.J.; Anthony J. Silvestri, Morrisville, Pa.

[73] Assignee: Mobil Oil Corporation, New York, N.Y.

[*] Notice: The portion of the term of this patent subsequent to July 8, 1992, has been disclaimed.

[21] Appl. No.: 686,445

[22] Filed: May 13, 1976

Related U.S. Application Data

[63] Continuation-in-part of Ser. No. 387,222, Aug. 9, 1973, Pat. No. 3,894,106, and a continuation-in-part of Ser. No. 537,043, Dec. 27, 1974, abandoned.

[51] Int. Cl.$^2$ .............................................. C07C 1/24
[52] U.S. Cl. ................................................... 260/682
[58] Field of Search .......................................... 260/682

[56] References Cited

U.S. PATENT DOCUMENTS 3,894,106   7/1975   Chang et al. ................... 260/673 X

FOREIGN PATENT DOCUMENTS 186,444   10/1966   U.S.S.R. ............................. 260/682

*Primary Examiner*—Delbert E. Gantz
*Assistant Examiner*—J. Thierstein
*Attorney, Agent, or Firm*—Charles A. Huggett; Carl D. Farnsworth

[57] ABSTRACT

A method and sequence of process steps is described for effecting the conversion of lower alcohols comprising methanol, ethanol, and propanol to primarily olefin boiling range component under conditions to significantly extract reaction heat and selectively control the restructuring of the alcohol feed through the production of ethers and particularly olefins.

6 Claims, No Drawings

CONVERSION OF METHANOL TO OLEFINIC COMPONENTS

This application is a continuation-in-part of application Ser. No. 387,222 filed Aug. 9, 1973 and now U.S. Pat. No. 3,894,106 and a continuation-in-part of application Ser. No. 537,043 filed Dec. 27, 1974 now abandoned.

BACKGROUND OF THE INVENTION

DESCRIPTION OF THE PRIOR ART

U.S. Pat. No. 3,036,134 to Mattox discloses the conversion of methanol to a reaction product containing water and dimethyl ether in the presence of, as a catalyst, a crystalline aluminosilicate.

Copending application Ser. No. 387, 223, filed Aug. 9, 1973 and now U.S. Pat. No. 3,894,107 discloses the conversion of alcohols and other similarly substituted simple hydrocarbon compounds to a reaction product containing water and highly aromatic, gasoline boiling-range hydrocarbons, by contacting such reactant with a crystalline aluminosilicate having a silica to alumina ratio of at least about 12 and contrast index, as there defined, of about 1 to 12.

Copending application Ser. No. 387,222, filed Aug. 9, 1973 and now U.S. Pat. No. 3,894,106, discloses the conversion of ethers to a reaction product contaiing water and gasoline hydrocarbons by contacting such with similarly defined catalyst.

The applicable class of catalysts is exemplified by ZSM-5, ZSM-11, ZSM-12, ZSM-21, and TEA Mordenite.

U.S. Pat. NO. 3,702,886 issued Nov. 14, 1972 to Argauer et al. discloses ZSM-5 zeolite catalyst.

U.S. Pat. No. 3,709,979 issued Jan. 9, 1973 to Chu discloses ZSM-11 zeolite catalyst.

West German Auslegeschrift No. 2213109 discloses ZSM-12 catalyst.

Copending application Ser. No. 358,192, filed May 7, 1973, now abandoned discloses ZSM-21 catalyst.

Copending application Ser. No. 130,442, filed Apr. 11, 1971, now abandoned discloses TEA Mordenite.

Although the above-described conversions perform exceptionally well and are usually effective at converting various non-gasoline organic chemicals to high quality gasoline, it has been found that these conversions are exothermic to varying degrees depending on the particular reactant. For example, the amount of heat generated in the conversion of the lower alcohols to hydrocarbon product may be estimated to be in the ranges shown:

| Alcohol Reactant | Heat Produced, BTU per lb. of Hydrocarbon Product |
| --- | --- |
| Methanol | 1300–2000 |
| Ethanol | 270–620 |
| Propanol | 20–360 |

While it is desirable that a reaction be exothermic, since this obviates the need for an external source of heat to drive the reaction, large heat generation loads can require substantial investment in complex reactors with extensive internal cooling means, thereby detracting from the overall economic efficiency of the process. It can be seen from the above table that the conversion of methanol, and to a lesser degree of ethanol, could be considered excessively exothermic in this regard. Furthermore, because of the inherent character and efficiency of the above described crystalline aluminosilicate zeolite catalysts, the reaction of methanol, and to a lesser degree of ethanol, tend to be self-accelerating, thereby creating excessively hot local regions, where the reaction tends to go to completion, in the catalyst bed. Thus, the simple expendient of conducting the reaction partially in a first catalyst bed and completing it in a second catalyst bed is not always available to facilitate heat removal. Additionally, it is generally good engineering practice to conduct reactant conversions at elevated pressures to more effectively utilize the reactor volume and process recovery of the reactor effluent. With a methanol charge, however, elevated pressures tend to produce increased quantities of 1, 2, 4, 5 tetramethylbenzene (durene). This product is believed to result at least in part from the mixing and reaction of yet-unconverted methanol with aromatic hydrocarbon products. In some situations, for example, when it is desired to utilize the conversion products as gasoline or to manufacture benzene, toluene and xylenes, durene is an undesirable by-product.

SUMMARY OF THE INVENTION

The present invention is concerned with a method of using multiple stages of catalyst compositions arranged for the controlled and segmented conversion or restructuring of methanol to olefin boiling components. More particularly, the present invention is directed to an arrangement and sequence of processing steps for more effectively and efficiently controlling the exothermic heat generated during the catalytic restructuring of lower alcohols such as methanol to olefins. The selective reaction stages herein contemplated proceed through methanol conversion to dimethyl ether or start with an ether feed from any source through conversion of ethers to olefins. Conversion of the olefins to gasoline boiling components may also be practiced. In a more particular aspect, the present invention is concerned with the exothermic temperature environment and catalyst restrictions required to more selectively control exothermic heat producing reactions encountered during conversion of, for example, dimethyl ether to particularly olefin boiling components. In one embodiment the present invention is particularly concerned with using a ZSM-5 crystalline zeolite for the conversion of ether products of the lower alcohols to olefins or gasoline boiling components comprising aromatics and isoparaffins.

DETAILED DESCRIPTION OF INVENTION

The lower alcohols that may be charged to the process of this invention, or more specifically to the first stage of a combination operation, include methanol, ethanol, propanol, and isopropanol. The feed may consist of a relatively pure single alcohol, or mixtures of these alcohols with other components such as higher alcohols. In general, any mixture comprising: methanol; or ethanol; or propanol; or isopropanol; and which is convertible with high exothermicity, is a suitable feed for the first stage of the present invention. Conversions which produce more than about 100 BTU/lb of total hydrocarbon product, and preferably more than about 200 BTU/lb of hydrocarbon product, at conversion temperature, are considered highly exothermic for the purpose of the present invention.

The preferred charges to the first stage of the present invention are ethanol and methanol. Particularly preferred are charges comprising substantial fractions, i.e. more than 25 weight percent, of methanol. Mixtures of methanol and dimethyl ether are included as preferred charges.

In the first stage of the present invention the alcohol reactant is contacted with a condensation catalyst to produce water and a predominantly aliphatic organic intermediate product. The condensation catalyst may be any catalyst which results in the intermolecular dehydration of the alcohol reactant to form an aliphatic product of higher carbon to oxygen ratio than the feed.

The condensation reactions contemplated include those that form simple and mixed ethers such as: dimethyl ether, diethyl ether, di-n-propyl ether, diisopropyl ether, methyl ethyl ether, methyl n-propyl ether, methyl isopropyl ether, ethyl n-propyl ether, ethyl isopropyl ether, and n-propyl isopropyl ether. All of these intermediates may be formed by the intermolecular dehydration of corresponding alcohol reactants, and all of these condensations are exothermic and generate heat. While this condensation reaction by itself, is generally known with alumina compositions, such as gamma alumina, it is noted that other acidic catalysts known in the art are very effective for the conversion. Such catalysts include, by way of example, liquid acids such as sulfuric and phosphoric acids, and solid inorganic and organic acidic catalysts such as phosphoric acid supported on kieselguhr, high surface area silica-alumina, acidic aluminas, acid treated clays, bauxites, and polystryrene sulfonic acids of the ion-exchange type including the macroreticular variety. For the purpose of this invention, it is preferred to use solid acidic catalysts.

Intramolecular dehydration reactions, such as the dehyration of ethanol to ethylene and water, and of propanol or isopropanol to propylene and water, although they form water and an aliphatic intermediate that has a higher carbon to oxygen ratio than the feed, these dehydration reactions are endothermic rather than exothermic.

Those skilled in the art will recognize that with methanol feed, no intramolecular dehydration is possible, and that therefore the condensation reaction can only proceed exothermally to form, for example, dimethyl ether. With ethanol, propanol, and isopropanol, on the other hand, the desired exothermic condensation and the undesired endothermic dehydration may occur over the same catalyst to different degrees under different conditions. For example, ethanol vapor passed over a certain solid acidic catalyst at about 212° F. will form, exothermically, diethyl ether; however, at substantially higher temperatures, ethanol will intramolecularly dehydrate to ethylene. In fact, over certain acidic catalysts, it is well known that a dehydrogenation reaction may set in at high temperature which not only does not split out water but is also endothermic.

In one embodiment, the combination operation of the present invention comprises sequential stages of catalytic contact in which combination the first stage is a catalyst restricted exothermic heat generating operation and the second catalyst stage is exothermically one combination of the operation herein described. The first stage operation is performed in the presence of a catalytic restructuring or conversion operation which is catalytically exothermic heat generating limited by restricting the conversion of methanol to approximately an equilibrium mixture comprising dimethyl ether, methanol and water. During this first stage limited conversion operation performed with a mass of catalyst suitable for the purpose such as gamma alumina, the reactant material conversion product or first stage reaction effluent mixture is temperature raised by the catalytically generated exothermic heat to about 600° F. or 650° F. The first stage reaction effluent mixture thus formed is adjusted to a temperature within the range of 600° F. to about 800° F. by passing through an indirect heat exchange zone in indirect heat exchange relationship with a circulating heat exchange fluid. For example, the heat exchange fluid may be water of the methanol reactant passed to the first catalyst conversion stage.

The second stage catalytic conversion operation of this invention is particularly restricted to converting a dimethyl ether feed from any source or the first stage effluent mixture comprising methanol, dimethyl ether and water to an olefin rich product material and/or a product rich in gasoline boiling components. The operation is highly exothermic and depending on the product desired occurs over a range of conditions but rapidly in the presence of selected crystalline zeolites and particularly a catalyst comprising a ZSM-5 type crystalline zeolite.

The class of zeolites in the process of this invention other than the first catalyst stage has some unusual properties. These zeolites by themselves can transform aliphatic hydrocarbons to aromatic hydrocarbons in commercially desirable yields. Although they have unusually low alumina contents, i.e., high silica to alumina ratios, they are very active even when the silica to alumina ratio exceeds 30. In fact product advantages during the formation of aromatics has been found by limiting the silica to alumina ratio below 60 therey reducing the formation of durene and permitting the use of higher pressures. The activity and selectivity characteristics of these crystalline zeolites are somewhat surprising since the alumina in the zeolite framework is believed responsible for catalytic activity. They retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity.

An important characteristic of the crystal structure of the class of zeolites particularly suitable for use herein is that the zeolite provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention, possess, in combination: a silica to alumina ratio of at least about 12; with some improved results obtained when using a silica to alumina ratio in the range of 30 to 70 to reduce the formation of durene and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolite useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these zeolites ineffective. Twelve-membered rings do not generally appear to offer sufficient constraint to produce the advantageous conversions, although structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of hydrocarbon per volume of catalyst per hour) over the catalyst with a helium dilution to give a helium a total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index from 1.0 to 12.0, preferably 2.0 to 7.0.

The class of zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in West German Offenlegunschrift 2,213,109, the entire contents of which are incorporated herein by reference.

ZSM-21 is more particularly described in U.S. application, Ser. No. 358,192, filed May 7, 1973, now abandoned, the entire contents of which are incorporated herein by reference.

TEA mordenite is more particularly described in U.S. application Ser. No. 130,442 filed Apr. 11, 1971, now abandoned, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does not appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalysts by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and TEA mordenite, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst. For example, a completely sodium exchanged H-ZSM-5 is not operative in the present invention.

In a preferred aspect of this invention, the catalysts hereof are selected as those having a crystal density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Struture by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

A remarkable and unique attribute of this type of zeolite is its ability to convert paraffinic hydrocarbons of aromatic hydrocarbons in exceptionally fine, commercially attractive yields by simply contacting such paraffins with such catalyst at high temperatures of about 800° to 1500° F. and low space velocities of about 1 to 15 WHSV. ZSM-5 type of zeolite seems to exert little or no action upon aromatic rings present in the feed to such process or formed in such process from the point of view of destroying (cracking) such rings. It does however have the ability with or without the presence of a special hydrogen transfer functionality and with or without the presence of added hydrogen in the reaction mixture, to cause paraffinic fragments, which presumably have been cracked from paraffinic feed components, to alkylate aromatic rings at somewhat lower temperatures of up to about 800° to 1000° F. It appears that the operative ranges for alkylation and formation of new aromatic rings overlap but that the optimum ranges are distinct, aromatization being at a higher temperature. The exact mechanisms for these catalytic functions are not fully known or completely understood.

It is generally known to those of routine skill in the crystalline zeolite art, that catalytic properties therof are often diminished by contact with steam. Increasing the steam pressure, temperature and/or time of contact of the zeolite with the steam increases the diminution of catalytic properties.

It is known that many acid catalysts are capable of assisting in the dehydration of ethers to olefins. In all or at least most of these prior processes, the dehydrated product had a longest carbon atom chain length which was not longer than the longest carbon atom chain length of the reactant. For the most part, such dehydration reactions did not produce products having a molecular weight in any given hydrocarbon portion which was higher than the molecular weight of a corresponding hydrocarbon portion of the ether reactant.

One aspect of this invention lies in the discovery that aliphatic ethers are convertible to other organic chemical products, notably aromatic hydrocarbons, by contacting such ethers with a crystalline aluminosilicate molecular sieve zeolite having a silica to alumina ratio of at least about 12 and a constraint index of about 1 to 12 at elevated temperatures, preferably about 500° to 1000° F., a pressure of about atmospheric to 3000 psig, a space velocity of about 0.5 to 1000 WHSV in the presence or absence of added hydrogen. The catalyst may be the zeolite alone or in the suitable matrix. The zeolite preferably has a crystal density in the hydrogen form of not substantially below about 1.6 grams per cubic centimeter. The ether reactant is preferably one or more alkyl ethers having one (1) to eight (8) carbon atoms in the longest hydrocarbon constituent thereof. Mixed ethers are suitable.

In one aspect, the reactive feed to the process hereof is critically defined as consisting essentially of lower aliphatic ether compounds. This feed definitions is specifically intended to distinguish from feeds used in alkylation reactions catalyzed by this type of synthetic aluminosilicate molecular sieve. In such alkylation reactions, which are considered to be the invention of other than the instant applicants, alkylating moieties, which may be ethers and/or other compounds, are reacted with the preformed and cofed aromatic moieties. In other words, alkylation requires the co-feeding of aromatic moieties and alkylating moieties such as ethers. The instant process is to be distinguished in that it does not require or desire the cofeeding of preformed aromatic moieties.

In this regard, two very important points must be emphasized: In the first place, it has now been discovered that the presence of preformed aromatic moieties as a co-feed to this reaction does not negate the armoatization conversion of the reactants designated above as the feed to the instant process; in the second place, new aromatic moieties created from the reactants hereof by the conversion process of this invention are themselves sometimes alkylated under these processing conditions by the alkylating action of the ether and/or one or more intermediate moiety formed in the reaction being undergone. The process of this invention must therefore be distinguished from an alkylating reaction per se carried out with the same catalyst and under co-extensive reaction conditions.

In its broadest aspects, this invention envisions a process for condensing certain feed materials and growing the products thus formed into significantly different chemical moieties. A commercially important aspect of this invention resides with the conversion of lower alkyl ethers to aromatic compounds as aforesaid. However, as an adjunct to this conversion, the conversion of the lower ethers can be carried out under different conditions but with the same catalyst to produce somewhat different chemical values. For example, the lower alkyl ethers can be converted particularly to olefins at somewhat lower temperatures and generally less severe operating conditions than those which result in a predominantly aromatic product.

While at first glance the formation of olefins by contacting ethers with an acidic zeolite at elevated temperatures might not seem too surprising, it must be pointed out that the olefins formed do not necessarily conform to the carbon configuration of the reactant. The olefin may and often does have a longer carbon to carbon chain than did the reacting moiety from which it was derived, including multiples of the reactant carbon chain length. It is even more surprising that one can produce olefins such as ethylene, propylene and butylene from methyl ethers, particularly dimethyl ether, that is effectively a one carbon atoms reactant.

In one aspect of this invention, aromatics are produced from lower aliphatic ethers at about 500° to 1000° F., 0 to 3000 psig and 0.5 to 50 LHSV. In yet another aspect, olefin production seems to predominate under less severe conditions such as by reduced contact time obtained by operating at space velocities in the range of 10 to 2000 LHSV and preferably in the range of 50 to 1000 LHSV at an operating temperature of about 700° F. Higher operating temperatures tend to promote the formation of aromatics but can offset to some considerable extent by using the higher space velocities. Suitable reactants include dimethyl ethyl, diethyl ether, methyl ethyl ether, methyl vinyl ether, isopropyl ether, n-butyl methyl ether, di-n-hexyl ether, methyl-2-ethyl hexyl ether, cyclohexyl methyl ether, etc.

It is within the scope of this invention to convert the ether compounds fed as individuals or as admixtures of normal chemical purity. It is also within the scope of this invention to feed such ether reactants in admixture with other, non-ether materials such as alcohols or carbonyl compounds. These other feed materials may be reactive or inert under the conditions of this process.

It is generally believed by those knowledgeable in the crystalline zeolite art that contact of a zeolite with steam is deleterious to the catalytic properties thereof and that an increase in pressure temperature and/or time of contact increases the adverse effects on the catalyst. While certain types of zeolites, notably ZSM-5 type, are substantially more steam stable than other zeolites, it has been found to be possible to reduce or eliminate the hydrocarbon aromatization catalytic activity. Aromatization of aliphatic hydrocarbons as described in application Ser. No. 253,942 filed May 17, 1972 now U.S. Pat. No. 3,756,942 has been attempted using this type of catalyst which had been previously severely steam treated. It was found to be substantially impossible to aromatize paraffinic hydrocarbons as set forth in such Application with such steamed catalyst. It is of interest to note, however, that such steamed catalyst is still quite active for aromatizing ether reactants. An additional unexpected aspect of this invention resides in the discovery that, although it is usual and common for conversion reactions carried out in the presence of and in contact with zeolite catalysts in general to form coke and deposit such on the zeolite catalyst thereby gradually deactivating the catalyst, the coke make deposited on the catalyst of this inventon in the process of this invention is exceedingly small, much smaller than that encountered when subjecting corresponding hydrocarbon feeds to the same conversion conditions.

It is interesting to note that while aromatizaton of hydrocarbons, even unsaturated hydrocarbons, is initiated to a meaningful extent of about 650° F. and is maximized from a commercially desirable product distribution point of view at about 1000° F., aromatization of lower ethers to generally the same commercially acceptable product distribution initiates at about 500° F. and is maximized at about 700° F. Contacting aliphatic hydrocarbons with this type of aluminosilicate zeolites in the same temperature and other operating condition ranges as set forth above according to this invention does not induce significant production of new aromatic rings but more usually tends to alkylate preformed, co-fed aromatic ring moieties. In this regard it should be understood that there is not a clear line of demarcation between operating conditions which induce alkylation as opposed to aromatization of fed aliphatic hydrocarbons according to previously described processes. Similarly, there is not a clear line of demarcation in product distribution as a function of temperature in the process of this invention. It can be said in general that lower temperatures favor olefin formation and higher temperatures, which are still generally lower than hydrocarbon aromatization temperatures, favor aromatization. Also the space velocity or reactant residence time in contact with the catalyst will affect these reactions.

The following Examples are illustrative of various aspects of the invention without being limiting on the scope thereof. Parts and percentages are by weight unless expressly stated to be the contrary.

EXAMPLES 1–4

In each example the catalyst used was 65% H ZSM-5 in an alumina matrix which was pelletized to 30/60 mesh size. The reactor was of the downflow type. The feed was dimethyl ether, the temperature of reaction 700° F., and the space velocity was 1.65 in Example 1 and 1.44 WHSV in the remaining examples. Pressures were 1, 5.5, 25 and 50 atmospheres respectively to induce conversions of 99.9+, 99.2, 99.3 and 98% respectively. The product distribution is set forth in the following Table:

TABLE

| Example No. | 1 | 2 | 3 | 4 |
|---|---|---|---|---|
| Hydrocarbon Product Distribution (%) | | | | |
| $C_4-$ | 40.94 | 28.84 | 26.40 | 25.44 |
| $C_5+$ Aliphatic | 17.62 | 33.83 | 37.18 | 35.12 |
| $C_6+$ Aromatics | 41.44 | 37.33 | 36.42 | 39.38 |

The process of this invention can be carried out in rather conventional up-flow or down-flow reactors packed with ZSM-5 type of aluminosilicate zeolite catalyst. The zeolite catalyst suitably occupies about 1 to 100% of the reaction zone volume and may be used in a fixed or fluidized bed arrangement. Suitable heating and/or cooling means may be employed according to conventional reaction zone temperature profiling design. The catalyst is suitably of a particle size of about 4 to 325 mesh.

EXAMPLE 5

This example illustrates the conversion of dimethyl ether to (predominantly) olefins.

| T | 800° F. | Catalyst 65% H ZSM-5/35% $Al_2O_3$ | |
|---|---|---|---|
| P | 1 atm. | | |
| WHSV | 428 | | |
| Conversion per pass | 23.1% | | |
| Hydrocarbon Product Distribution (%) | | | |
| Olefins | | $C_2=$ | 13.63 |
| | | $C_3=$ | 29.57 |
| | | $C_4=$ | 18.39 } 67.81 |
| | | $C_5=$ | 6.22 |
| Paraffins | | $C_1 - C_5$ | 19.07 |
| Non-aromatic | | $C_6+$ | 6.79 |
| Aromatics | | | 6.33 |

EXAMPLE 6

Di-n-hexyl ether

T = 700° F
P = 1 atm.
WHSV = 1.26
Catalyst 65% H-ZSM-5/35% $Al_2O_3$ (1/16" extrudate)
Conversion 100%

Hydrocarbon Product Distribution (%)

| | | |
|---|---|---|
| | $C_4-$ | 49.18 |
| Aliphatic | $C_5+$ | 13.12 |
| Aromatics | $C_6+$ | 37.70 |

EXAMPLE 8

Tetrahydrofuran

T = 700° F.
P = 1 atm.
WHSV = 1.39
Catalyst 65% H ZSM-5/35% Al$_2$O$_3$ (1/16" extrudate)
Conversion 99.3%

Hydrocarbon Product
Distribution (%)

|  | C$_4$− | 27.41 |
|---|---|---|
| Aliphatic | C$_5$+ | 6.43 |
| Aromatic | C$_6$+ | 66.16 |

CH$_3$O CH$_2$O CH$_3$ (methylal)

T = 700° F.
P = 1 atm.
WHSV = 1.35
Catalyst 65% H ZSM-5/35% Al$_2$O$_3$ (1/16" extrudate)
Conversion 100%

Hydrocarbon Product
Distribution (%)

|  | C$_4$− | 41.65 |
|---|---|---|
| Aliphatic | C$_5$+ | 10.27 |
| Aromatic | C$_6$+ | 48.08 |

In a conversion operation involving methanol and/or dimethyl ether to form olefins in the presence of catalysts such as ZSM-5 type zeolites, TEA mordenite and de-aluminized erionite (see Examples 5, 8 and 9), it has been observed that high selectivity to light olefins is particularly achieved at low conversions per pass and restricted to within the range of 5 to about 25. In a typical operation, methanol is first converted to DME (dimethyl ether) over gamma alumina catalyst. The DME is then passed in contact with ZSM-5 type crystalline zeolite at a space velocity selected from within the range of 50 to 1000 LHSV under a pressure condition selected from within the range of atmospheric up to about 100 psi and a temperature selected from within the range of 500 to about 900° F. Within these operating conditions of restricted conversion the DME is converted to olefins and the exothermic heat of reaction can be removed by substantially any suitable method and/or means.

High LHSV (liquid hourly space velocity) may be obtained in a variety of ways including tubular reactors provided with suitably spaced catalyst particles and fluid catalyst systems such as dense and dispersed catalyst phase relatively short riser catalyst systems. Also thin fixed bed or fluid catalyst bed systems may be relied upon to provide the high velocity short contact time conditions particularly desired for olefin production. In any of these process configurations, a portion of the exothermic reaction heat may be removed by catalyst circulation and recycling of unconverted feed such as methanol and/or DME to provide a sensible heat carrying medium. Thus, since the conversion per pass is kept quite low below 25 percent for olefin product, there is a considerable amount of unconverted feed available for recycling, and thus maximum utilization of the feed for the purpose intended. Recycle to fresh feed ratio are relatively high and usually in the range of 6 or 8 to 1. The actual amount of recycle used in dependent upon the operation heat balance and space velocity employed. In a suitable recovery system, C$_2$ and C$_3$ olefins are isolated by distillation and separated from heavier materials including hydrocarbons and water. The unreacted methanol and/or DME feed is taken as recycle from the recovery system and recycled to the reactor.

EXAMPLE 9

OLEFIN PRODUCTION FROM DIMETHYL ETHER (DME) OVER HZSM-5 AT 700° F. 1 atm.

| Run No. | SSA 133B | SSA 135B |
|---|---|---|
| LHSV | 1080 | 360 |
| Conversion % | 6.1 | 11.3 |
| Hydrocarbon Composition, wt.% | | |
| Methane | 1.9 | 2.0 |
| Ethane | — | — |
| Ethylene | 20.4 | 27.0 |
| Propane | — | — |
| Propylene | 64.8 | 63.0 |
| Butanes | 12.9 | 4.0 |
| Butenes | — | — |
| C$_5$+ | — | 3.1 |

Having thus generally described the various aspects of the present invention and presented examples in support thereof, it is to be understood that no undue restrictions are to be imposed by reasons thereof except as defined by the following claims

We claim:

1. A method for producing olefins from a feed selected from the group consisting of lower alcohols, one or more ether dehydration products of lower alcohols and mixtures of one or more lower alcohols and an ether derivative thereof which comprises passing said feed in contact with a crystalline aluminosilicate zeolite having a pore dimension greater than about 5 Angstroms, a silica to alumina ratio of at least about 12, and a constraint index of about 1 to 12, said contact being carried out at a temperature within the range of 500–900° F, a pressure from atmospheric up to about 100 psi, a space velocity of 50–1000 LHSV, said temperature and space velocity being selected within said ranges so as to restrict conversion of the feed within the range of 5 to 25%, and recovering an olefin product.

2. The method of claim 1 wherein unconverted feed is recycled at a recycle/fresh feed ratio in the range of 6–8/1.

3. The method of claim 1 wherein the velocity of the feed passed in contact with the catalyst is at least 100 LHSV.

4. The method of claim 1 wherein said aliphatic ether is dimethyl ether.

5. The method of claim 1 wherein said aliphatic ether-containing feed comprises dimethyl ethyl, water, and methanol.

6. The method of claim 1 wherein production of the olefin product is enhanced by operating at a reaction temperature below 800° F.

* * * * *